United States Patent
Zambianchi et al.

(10) Patent No.: US 7,736,516 B2
(45) Date of Patent: Jun. 15, 2010

(54) FILTER FOR THE REMOVAL OF SUBSTANCES FROM BLOOD PRODUCTS

(75) Inventors: Laura Zambianchi, Reggio Emilia (IT); Paolo Bonaguidi, Pisa (IT); Giorgio Mari, Mirandola (IT)

(73) Assignee: Fresenius Hemocare Italia S.r.l., Cavezzo (Modena) (IT)

( * ) Notice: Subject to any disclaimer, the term of this patent is extended or adjusted under 35 U.S.C. 154(b) by 1169 days.

(21) Appl. No.: 10/563,206

(22) PCT Filed: Jul. 1, 2004

(86) PCT No.: PCT/EP2004/007162

§ 371 (c)(1), (2), (4) Date: Jan. 3, 2006

(87) PCT Pub. No.: WO2005/002647

PCT Pub. Date: Jan. 13, 2005

(65) Prior Publication Data

US 2006/0169635 A1 Aug. 3, 2006

(30) Foreign Application Priority Data

Jul. 3, 2003 (EP) .................. 03015088

(51) Int. Cl.
| | |
|---|---|
| B01D 37/00 | (2006.01) |
| B01D 61/00 | (2006.01) |
| B01D 29/00 | (2006.01) |
| B01D 71/80 | (2006.01) |
| A61M 1/34 | (2006.01) |
| C08G 63/672 | (2006.01) |
| D01F 6/86 | (2006.01) |

(52) U.S. Cl. ............... 210/650; 210/252; 210/257.1; 210/500.1; 210/500.36; 210/651; 210/767; 604/403; 604/406; 604/408; 604/410

(58) Field of Classification Search ............. 210/500.1, 210/500.36, 252, 257.1, 650, 651, 767; 604/403, 604/406, 408, 410

See application file for complete search history.

(56) References Cited

U.S. PATENT DOCUMENTS

| | | | |
|---|---|---|---|
| 4,618,533 A | | 10/1986 | Steuck |
| 4,622,263 A | | 11/1986 | Ando et al. |
| 5,162,102 A | | 11/1992 | Nogawa et al. |
| 5,399,268 A | | 3/1995 | Pall et al. |
| 5,580,465 A | | 12/1996 | Pall et al. |
| 5,681,645 A | * | 10/1997 | Strack et al. .............. 428/196 |
| 6,166,168 A | | 12/2000 | Kuwahara et al. |
| 6,441,152 B1 | | 8/2002 | Johansen et al. |
| 2002/0000403 A1 | | 1/2002 | Tanaka et al. |
| 2003/0146150 A1 | | 8/2003 | Hayashi |
| 2004/0121678 A1 | * | 6/2004 | Baldwin et al. .............. 442/110 |

FOREIGN PATENT DOCUMENTS

| | | |
|---|---|---|
| EP | 0 313 348 A2 | 4/1989 |
| EP | 0 397 403 A1 | 11/1990 |
| EP | 1 156 067 A2 | 11/2001 |
| EP | 1 262 204 A1 | 12/2002 |

* cited by examiner

*Primary Examiner*—John Kim
(74) *Attorney, Agent, or Firm*—Jacobson Holman PLLC

(57) ABSTRACT

A filter for the removal of substances from blood product has a porous element of a polymeric material consisting of a polyether-ester copolymer or of a polymer blend comprising said copolymer.

19 Claims, No Drawings

FILTER FOR THE REMOVAL OF SUBSTANCES FROM BLOOD PRODUCTS

This is a nationalization of PCT/EP2004/007162 filed 1 Jul. 2004 and published in English.

The present invention relates to a microfilter for the removal of particles from blood or blood components and more particularly, to a leukocyte filter adapted for use in the blood purification devices, such as blood bag systems which are conventionally used for the separation of whole blood into leukocyte depleted hemocomponents.

The blood filters, to which the present invention relates, typically comprise a housing with inlet and outlet ports and at least a porous element, within the housing, interposed between the inlet and outlet port.

The porous element usually consists of a web which may be formed by one or more layers of filtering material, typically a non-woven fabric, which may or may not be bonded to each other.

According to the prior art, the porous elements can be produced from any material compatible with blood, which is capable of forming fibres including natural or synthetic fibres.

The preferred materials are synthetic polymers, such as particularly polyolefins, polyesters and polyamides.

Fibrous leukocyte filters are well-known in the prior art and are described e.g. in EP-A-0 313 348 and EP-A-0 397 403.

Preferred materials for use in leukocyte filters are synthetic resins, which are adapted to be processed into very fine fibres (with a diameter preferably lower than 3 μm) by melt-blowing.

The currently used preferred material is polybutyleneterephthalate (PBT). The surface properties of the employed fibre material can be modified to increase its wettability or its Critical Wetting Surface Tension (CWST), which is a measure of the hydrophilicity of the material.

To this end, fibres of a hydrophobic resin, such as PBT, have been coated with a more hydrophilic polymer, such as particularly hydrophilic acrylic polymers or copolymers or hydrophilic polyurethanes.

The polymeric material used for the fibres can also be rendered more hydrophilic by surface grafting the polymeric material, particularly PBT, with compounds containing an ethylenically unsaturated group, such as an acrylic moiety combined with hydroxyl groups or methylacrylate or methylmethacrylate and combinations thereof, as described in EP-A-0 313 348.

In general, a filter with a higher hydrophilicity is enhancing the recovery of platelets, as described in U.S. Pat. No. 5,580,465 and U.S. Pat. No. 4,618,533.

U.S. Pat. No. 5,162,102 describes a medical instrument, including a filter member comprising a screen mesh formed of a hydrophobic synthetic resin, such as polypropylene, polyethylene and polyester, which is coated with a non-ionic surface-active agent, such as preferably block copolymers of propylene oxide and ethylene oxide.

EP-A-1 156 067 describes a blood filter having a filter material, which is preferably a non-woven fabric of polyethyleneterephthalate (PET) or polybutyleneterephthalate (PBT), which is surface coated with a copolymer comprising an alkoxyalkyl(meth)acrylate and a co-monomer having a copolymerisable functional group such as amino, pyridyl, aziridine and imidazolyl.

The blood filter is described as suitable particularly for achieving high removal rates for leukocytes and platelets with low activation of blood components.

EP-A-1 262 204 describes a blood filter for selective removal of leukocytes comprising a polymer having a hydrophobic structural unit and a hydrophilic structural unit and a porous substrate.

Examples of hydrophobic monomers for forming the hydrophobic structural units include ester-type monomers, such as methacrylic acid esters and acrylic acid esters.

The preferable hydrophilic monomers for forming the hydrophilic structural units are N,N'-disubstituted acrylamides and N,N'-disubstituted methacrylamides.

Also in this case, the described polymer is coated onto a substrate which is preferably formed from fibres, such as PET fibres.

An object of the present invention is to provide novel polymeric materials, which are particularly suitable for the manufacturing of the porous element of a blood filter device.

A more specific object of the invention is to provide a polymeric material which can be processed into fine fibres, e.g. by melt-blowing, which have the appropriate hydrophilicity (CWST) for use in a blood filter, without the need of additional surface coating or surface grafting.

In view of the above mentioned objects, the invention provides a microfilter for the removal of substances from blood fluids, comprising a porous filtering element made of a polymeric material, characterised in that said polymeric material comprises a polyether-ester copolymer having hydrophilic and hydrophobic segments.

The invention is also directed to a method for filtering blood fluids, particularly for leukocyte removal, with the use of the novel filter of the invention and to a blood treatment or purification device, particularly a blood bag device for the separation of blood into leukocyte depleted blood components, including the filter of the invention.

The subject matter of the invention is defined in the appended claims.

The polyether-ester copolymer used according to the invention is obtained by polycondensation in the melt of at least one alkyleneglycol, at least one aromatic dicarboxylic acid or an ester thereof and a polyalkylene oxide glycol. The alkyleneglycol may contain 2-4 carbon atoms and the preferred glycol is butyleneglycol.

Suitable for use as aromatic dicarboxylic acid are particularly terephthalic acid, 1,4-naphtalenedicarboxylic acid and 4,4'-diphenyldicarboxylic acid.

Preferred polyalkylene oxide glycols include polybutylene oxide glycol, polypropylene oxide glycol and polyethylene oxide glycol or combinations thereof; particularly preferred is a block copolymer of polypropylene oxide (PPO)/polyethylene oxide (PEO).

The resulting polymer has a backbone built up of a hard segment (hydrophobic) of repeating units, derived from the alkyleneglycol (preferably 1,4-butandiol) and the aromatic dicarboxylic acid (preferably terephthalic acid or dimethylterephthalate) and a soft hydrophilic segment deriving from one polyalkylene oxide glycol.

A preferred resulting polymer structure is:

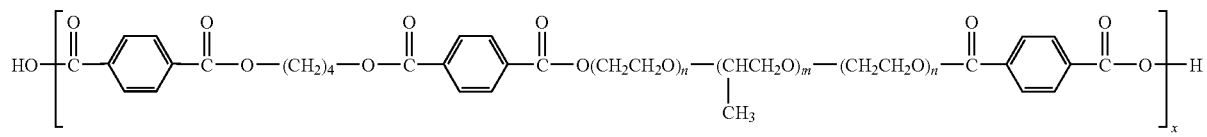

which, however, is not to be construed as limiting the present invention.

Suitable polyalkylene oxide glycols are commercially available, such as e.g. Pluronic PE6002™, which is polypropylene oxide end capped with ethylene oxide glycol from Basf (ethylene oxide:propylene oxide=36/64–weight ratio).

The copolyether esters of the invention are commercially available or can be prepared according to known polycondensation processes, preferably according to the process described in U.S. Pat. No. 6,441,125 by polycondensation in the melt of the above-mentioned components in the presence of a catalyst based on a combination of titanium and a bivalent metal in a single compound or a combination of titanium and a bivalent metal containing compounds, wherein the molecular ratio of titanium to the bivalent metal is preferably lower than 1.5.

The bivalent metals are preferably alkaline earth metals, preferably magnesium; titanium is preferably in the form of a metal organic compound, such as titanium alkoxide or a titanium ester.

Heretofore, leukocyte filters made from hydrophilic copolymer fibres have not been proposed, since the properties of copolymers were thought to be unsuitable for the "melt-blowing process" allowing to achieve fine fibres.

As the result of the invention, it has been found that the copolyether-ester herein described can be processed by melt-blowing to obtain fibres having a diameter in the range of less than 6 μm and preferably less than 3 μm; the preferred mean diameter being in the range from 1.8 to 2.2 μm.

It has been found that in order to improve processability by melt-blowing and to obtain fabrics having properties suitable for use in the filter of the invention, the amount of the polyalkylene oxide glycol in the copolyether ester is preferably in the range of from 0.1 to 20% by wt. or 0.03-6% by wt. of polyethylene oxide.

By varying the amount of polyalkylene oxide in the copolymer and/or the weight ratio between polypropylene oxide and polyethylene oxide (when block copolymer PPO/PEO is used), it is possible to obtain fabrics characterised by a range of CWST between 54-80 dynes/cm, which is useful for filtration of whole blood or blood components.

The fabric obtained with the material of the invention has textile properties which are similar to those of PBT fabric.

Within the scope of the invention, it is also contemplated the use of polymeric blends comprising the polyether-ester copolymer (as before described) and a thermoplastic polymer suitable to be processed by melt-blowing, particularly an aromatic polyester, preferably PET or PBT.

In the polymeric blends, the weight ratio between the copolyester-ether component and the aromatic polyester (preferably PBT) may range from 1:99 to 99:1; preferred polymeric blends comprise up to 40% by wt. of the copolyester-ether referred to the sum of copolyester-ether and aromatic polyester.

Fibres made of the copolyether-ester or polymeric blends as described, do not require additional surface coating or grafting; however, fibres according to the invention which are surface coated or grafted to further increase their hydrophilicity are comprised within the scope of the invention.

The filter of the invention can be used to advantage in any application relating to filtration of blood and blood components, particularly for the removal of leukocytes; the possibility of modifying the critical wetting surface tension by varying the amount of polyalkylene oxide in the copolyether-ester allows the production of a filter device including a plurality of filter elements, each made of a plurality of layers of filtering material, according to the invention, wherein the filter elements have a different hydrophilicity and particularly a decreasing hydrophilicity (decrease in CWST) from inlet to outlet of the filter device as described in TO2002A000820.

EXAMPLE 1

Comparative

Fabric Material
  Poly(butylenterephtalate) (PBT).

Fabric Production
  The fabric is produced from melt blown fibres having a mean diameter in the range from 1.8 to 2.2 μm.

Filter Preparation
  40 layers of the fabric are inserted in a conventional housing (surface area 50 cm²) having an inlet and an outlet port.

EXAMPLE 2

Fabric Material

The fabric material is a copolyether ester A obtained by polycondensation and having the following composition (% by wt.):
  terephthalic acid: 60%
  butandiol: 39%
  block copolymer polypropylene oxide (PPO)/polyethylene oxide (PEO): 1%
  The PEO content is 0.3%.

Fabric Production
  The fabric is produced from melt blown fibres having the same mean diameter as in example 1. The CWST of the fabric is 54 dynes/cm.

Filter Preparation
  40 layers of the fabric are inserted in the same housing (surface area 50 cm²) having an inlet and an outlet port of example 1.

EXAMPLE 3

Fabric Material

The fabric material is obtained by blending PBT and a copolyether ester B in a weight ratio 70/30.

The copolyether ester B is obtained by polycondensation and having the following composition (% by wt.):
terephthalic acid: 32%
butandiol: 15%
block copolymer polypropylene oxide (PPO)/polyethylene oxide: 53%
The PEO content in the blend is 4.4%.

Fabric Production

The fabric is produced from melt blown fibres having the same diameter of example 1. The CWST of the fabric is 72 dynes/cm.

Filter Preparation 40 layers of the fabric are inserted in the same housing (surface area 50 cm$^2$) having an inlet and an outlet port of example 1.

Blood Filtration

Whole blood (range 450-550 ml) was collected from random donors in a PVC bag with 70 ml of CPD. All whole-blood donations were cooled to 20-24° C. under 1,4 butanediol plates. The filtration was performed by gravity. The cell concentration was determined by an automatic analyser in the blood before filtration and in post filtration in order to determine the total platelet (PLT) removal percentage. White blood cells (WBCs) in the filtered blood were counted in a Nageotte haemocytometer.

TABLE 1

| | | | | | | |
|---|---|---|---|---|---|---|
| | | | | Filtration results | | |
| Es. | PEG/PEO % (w/w) | PEO % (w/w) | CWST dynes/cm | TEST No. | Filtration time (min) | PLT removal % | WBC/unit 10$^6$ |
| 1 | 0 | 0 | 52 | 10 | 30 | 99 | 0.7 ± 0.5 |
| 2 | 1 | 0.3 | 54 | 10 | 18 | 96 | 0.2 ± 0.1 |
| 3 | 1 | 4.4 | 72 | 10 | 16 | 55 | 0.5 ± 0.2 |

In Table 1 are compared the filtration results obtained with pure PBT (example 1) and the hydrophilic copolyether-ester containing different amounts of PEO (examples 2-3). The introduction of PEO in the fabric material (example 2) increases the ability to the filter material to remove leukocyte By increasing the PEO amount in the copolyether-ester (example 3) the PLT recovery increases and for this reason it is possible to use this fabric material in applications where it is important the recovery of PLT.

The invention claimed is:

1. A method for removing substances from blood products comprising feeding said blood products through a microfilter, the microfilter containing a porous element made of a polymeric material, wherein the polymeric material includes a polyether-ester copolymer having hydrophilic and hydrophobic segments, wherein the hydrophobic segments have repeating units derived from an alkyleneglycol and at least one aromatic dicarboxylic acid or ester thereof and at least one hydrophilic segment is derived from at least one polyalkylene oxide glycol.

2. The method according to claim 1, wherein the substance to be removed from the blood product is leukocytes and the blood product is selected from the group consisting of whole blood, platelet-rich plasma, packed red cells, platelet concentrate and plasma.

3. The method according to claim 1, wherein the aromatic dicarboxylic acid or ester thereof is terephthalic acid or an alkyl ester thereof.

4. The method according to claim 1, wherein the alkyleneglycol is selected from the group consisting of ethylene glycol, propylene glycol and butylene glycol.

5. The method according to claim 1, wherein the polyalkylene oxide glycol is selected from the group consisting of polyethylene oxide glycol, polypropylene oxide glycol and block copolymers propylene oxide/ethylene oxide.

6. The method according to claim 1, wherein the polyether-ester copolymer comprises from 0.1 to 20% by weight of polyalkylene oxide glycol.

7. The method according to claim 1, wherein the porous element is made of fibres of the polymeric material.

8. The method according to claim 7, wherein the porous element comprises a nonwoven fabric from the polymeric material.

9. The method according to claim 1, wherein the porous element is made of melt-blown uncoated fibres of the polymeric blend.

10. The method according to claim 1, wherein the porous element has a CWST in the range of from 50 to 80 dynes/cm.

11. A blood purification device comprising a microfilter, the microfilter containing a porous element made of a polymeric material, wherein said polymeric material comprises a polyether-ester copolymer having hydrophilic and hydrophobic segments, wherein the hydrophobic segments have repeating units derived from an alkyleneglycol and at least one aromatic dicarboxylic acid or ester thereof and at least one hydrophilic segment is derived from at least one polyalkylene oxide glycol,
the blood purification device further comprising a blood bag device for the separation of blood into leukocyte depleted blood components, the blood bag device including a first bag in fluid communication with a second bag via the microfilter.

12. The blood purification device of claim 11, wherein the aromatic dicarboxylic acid or ester thereof is terephthalic acid or an alkyl ester thereof.

13. The blood purification device of claim 11, wherein the alkyleneglycol is selected from the group consisting of ethylene glycol, propylene glycol and butylene glycol.

14. The blood purification device of claim 11, wherein the polyalkylene oxide glycol is selected from the group consisting of polyethylene oxide glycol, polypropylene oxide glycol and block copolymers propylene oxide/ethylene oxide.

15. The blood purification device of claim 11, wherein the polyether-ester copolymer comprises from 0.1 to 20% by weight of polyalkylene oxide glycol.

16. The blood purification device of claim 11, wherein the porous element is made of fibres of the polymeric material.

17. The blood purification device of claim 16, wherein the porous element comprises a nonwoven fabric from the polymeric material.

18. The blood purification device of claim 11, wherein the porous element is made of melt-blown uncoated fibres of the polymeric blend.

19. The blood purification device of claim 11, wherein the porous element has a CWST in the range of from 50 to 80 dynes/cm.

* * * * *